United States Patent
Chen et al.

[11] Patent Number: 6,088,092
[45] Date of Patent: Jul. 11, 2000

[54] GLASS SUBSTRATE INSPECTION APPARATUS

[75] Inventors: Li Chen, Fremont; Raj Chhibber, San Jose, both of Calif.

[73] Assignee: Phase Metrics, Inc., San Diego, Calif.

[21] Appl. No.: 09/337,142

[22] Filed: Jun. 21, 1999

[51] Int. Cl.[7] .................................................. G01N 21/00
[52] U.S. Cl. ..................... 356/237.2; 356/239.7
[58] Field of Search ............................. 356/237.1, 237.2, 356/237.3, 237.4, 237.5, 239.1, 239.2, 239.3, 239.7, 239.8; 250/559.4, 559.41, 559.42; 369/58, 112

[56] References Cited

U.S. PATENT DOCUMENTS

| | | | |
|---|---|---|---|
| 3,792,930 | 2/1974 | Obenreder | 356/239.1 |
| 3,857,637 | 12/1974 | Obenreder | 356/239.7 |
| 5,712,701 | 1/1998 | Clementi et al. | 356/237.2 |
| 5,875,029 | 2/1999 | Jann et al. | |

Primary Examiner—Hoa Q. Pham
Assistant Examiner—Sang Hoang Nguyen
Attorney, Agent, or Firm—Irell & Manella LLP

[57] ABSTRACT

An optical inspection station for inspecting a substrate. The substrate may include a first surface and a second surface. Light is reflected from both the first and second surfaces of the substrate. The light reflected from the first surface is detected by a light detector. A controller may determine a surface characteristic of the first surface from the detected light. The system may include a spatial filter that filters the light reflected from the second surface. The spatial filter eliminates the optical noise that may be created by the light reflected from the second surface.

11 Claims, 3 Drawing Sheets

GLASS SUBSTRATE INSPECTION APPARATUS

BACKGROUND OF THE INVENTION

1. Field of the Invention

The present invention relates to an optical inspection station that can inspect the surface of a substrate, such as the glass substrate of a magnetic hard disk.

2. Background Information

Hard disk drives contain a number of magnetic transducers that are coupled to the surfaces of rotating magnetic disks. The transducers can magnetize and sense the magnetic fields of the disks to write and read data as is known in the art. The data is typically stored within concentric annular tracks on the disks.

The transducers are typically integrated into a head that is gimbal mounted to an actuator arm. The actuator arm may include a voice coil motor that can move the heads to the various tracks of the disks.

Each head has an air bearing surface that cooperates with the air flow generated by the rotating disks to create an air bearing between the transducers and the disk surface. The air bearing prevents mechanical wear between the head and the disk surface. It is desirable to optimize the height of each air bearing to maximize the magnetic coupling between the disk surface and the transducers, while preventing mechanical wear between the components.

It is desirable to inspect the disk to insure that there are no defects in the disk surfaces. Defects such as bumps may cause undesirable contact with the heads. There have been developed a number of different inspection systems that can inspect the disk surfaces. For example, U.S. Pat. No. 5,875,029 issued to Jann et al. discloses an optical inspection station that reflects light from a disk surface. The Jann system contains light detectors that can detect the reflected light. The detectors provide input to a computer that can determine the surface characteristics of the light from the detected light.

A magnetic disk typically contains an aluminum substrate that is coated with different layers of magnetic material. There have also been developed magnetic disks that contain a glass substrate. It is desirable to inspect the glass substrate before applying the layers of magnetic material to increase the yield and reduce the cost of producing the disks. It has been found that reflecting light from a glass substrate will produce two images, an image of the top surface and an image of the bottom surface. The image from the bottom surface creates optical noise that distorts the top surface image and degrades the accuracy of the inspection system. It would be desirable to provide an optical inspection system that can more effectively inspect glass substrates than systems of the prior art.

SUMMARY OF THE INVENTION

An embodiment of the present invention may include an optical inspection station for inspecting a substrate. The substrate may include a first surface and a second surface. Light is reflected from both the first and second surfaces of the substrate. The light reflected from the first surface is detected by a light detector. The light reflected from the second surface may be filtered by a spatial filter. A controller may determine a surface characteristic of the first surface from the detected light.

DETAILED DESCRIPTION

Figure 1:
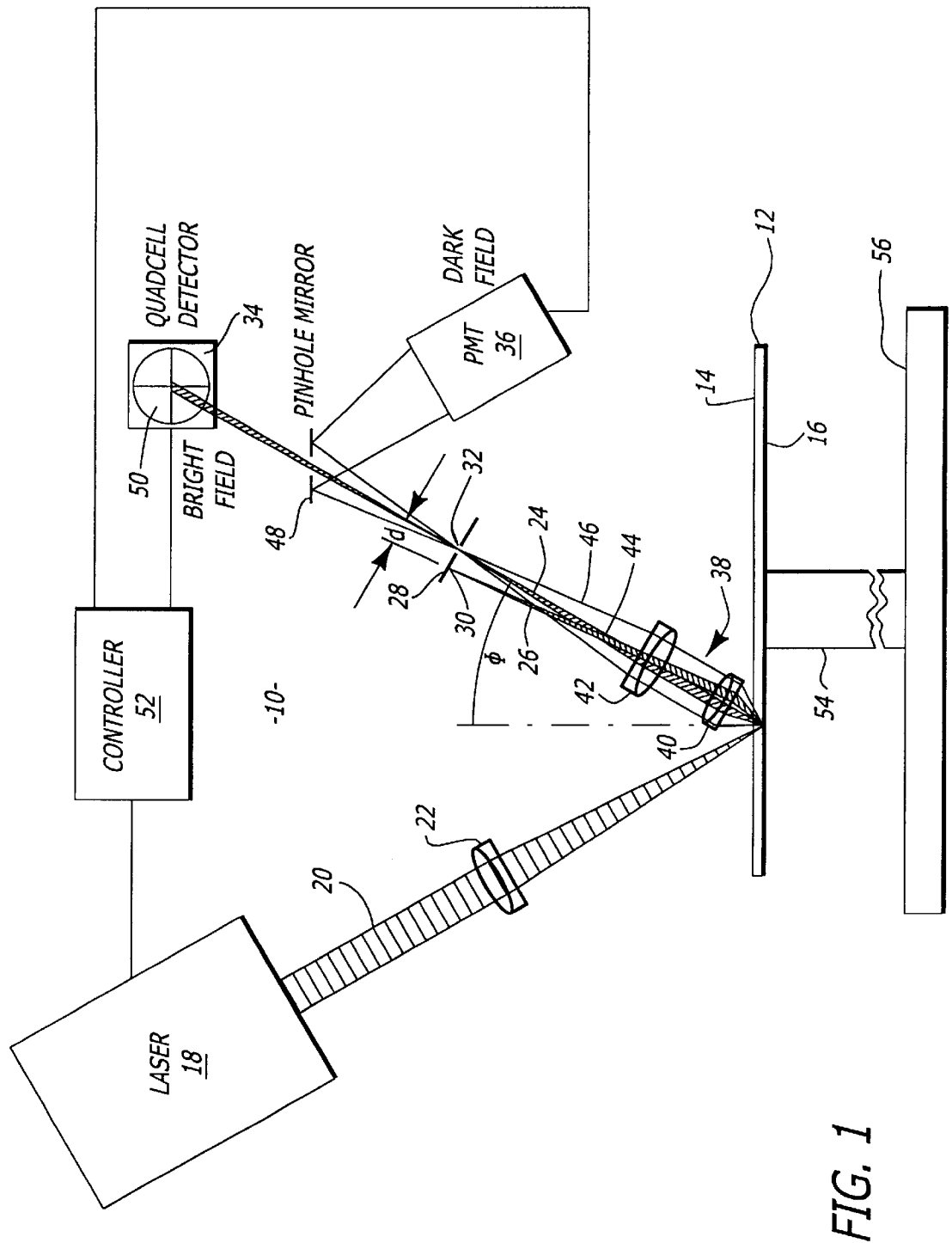
FIG. 1 is a schematic of an embodiment of an optical inspection station of the present invention.

Referring to the drawings more particularly by reference numbers, FIG. 1 shows an embodiment of an optical inspection system 10 of the present invention. The system 10 can be used to inspect a substrate 12 that has a first surface 14 and an opposite second surface 16. The substrate 12 may be constructed from an optically transparent material such as glass. By way of example, the glass substrate 12 may be subsequently coated with magnetic material after inspection to form a magnetic disk that is assembled into a hard disk drive. Although a glass substrate for a magnetic disk is shown and described, it is to be understood that the inspection station 10 can be used to inspect any optically transparent material. Additionally, the optical inspection station can also be used to inspect the surface of an object that is not optically transparent. For example, the same inspection station 10 can also be used to inspect the substrate 12 after magnetic material has been applied to the surfaces 14 and 16.

The system 10 may include a light source 18 that reflects a light beam 20 from the substrate 12. The light source 18 may be a laser that emits monochromatic light. The light beam 20 may be focused onto the substrate by a lens 22. The lens 22 may be configured to create an elliptical spot on the substrate 12. An elliptical spot can cover more surface area and thus reduce the time required to inspect the substrate 12. The elliptical spot may be generated using the structure(s) and technique(s) disclosed in U.S. Pat. No. 5,719,840 issued to Jann, which is hereby incorporated by reference.

The substrate 12 reflects a portion of the light 24 from the first surface 14 and a portion of light 26 from the second surface 16. It is desirable to filter the light reflected from the second surface 16 to reduce the optical noise for the light reflected from the first surface 14. The system 10 may include a spatial filter 28 to filter all or a portion of the light 26 from the second surface 16. The spatial filter 28 may be a stop that has an opaque portion 30 that prevents further transmission of the light 26. The stop may also contain an aperture 32 that allows the light 24 to transmit to a first light detector 34 and a second light detector 36.

The system 10 may include a lens assembly 38 that directs the light 24 from the second surface 16 onto the opaque portion 30 of the stop while focusing the light 24 from the first surface 14 into the aperture 32. The lens assembly 38 may include a first lens element 40 and a second lens element 42. Although two lens elements 40 and 42 are shown and described, it is to be understood that the lens assembly 38 may have any number of lens elements including an assembly with just one lens.

Because of refraction through the substrate 12, the light reflected from the second surface 16 will be introduced to the lens assembly 38 at a different angle than the light 24 reflected from the first surface 14. The different angle will result in a different focal point for the light 26 than the light 24. The lens assembly 38 can be constructed to focus the light 24 into the aperture and the light 26 onto the opaque portion 30 depending upon various factors including the incident angle $\Phi$ of the light beam 20, the thickness of the substrate 12 and the index of refraction of the substrate 12.

Figure 2:
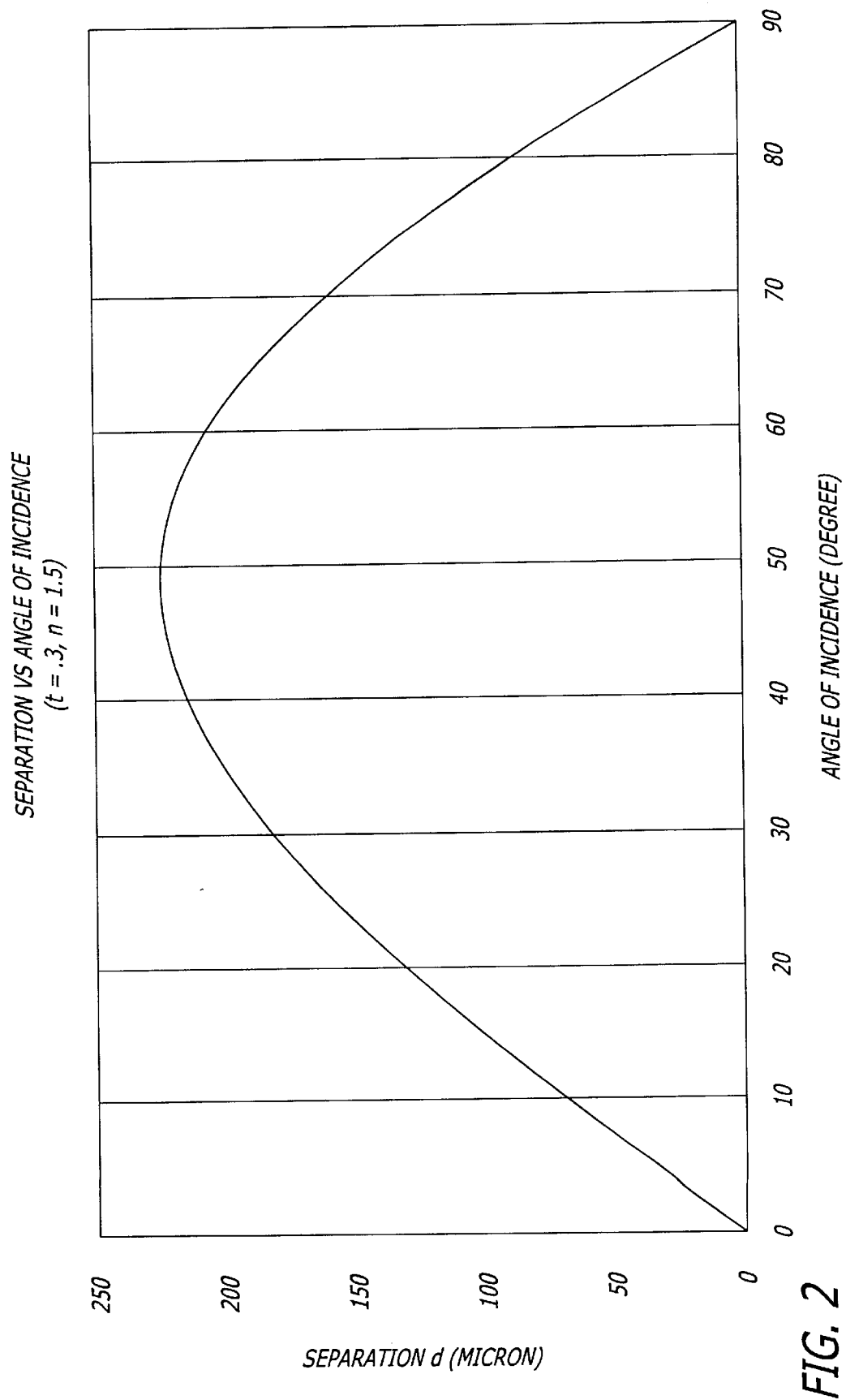
FIG. 2 is a graph showing the separation between light reflected from a first surface of a substrate and light reflected from a second surface of the substrate versus the angle that the light is reflected from the substrate.

It is preferable to reflect the light from the substrate 12 at an oblique incidence angle Φ to filter a significant portion of the light 26 reflected from the second surface 16. FIG. 2 shows a graph of the separation d between the focal point of light 24 and the point at which the light 26 impinges the opaque portion 30. The graph was constructed with a glass substrate 12 having a thickness of 0.3 millimeters and an index of refraction of 1.5. As can be seen the farthest separation d is at an angle Φ of 50 degrees. It being understood that the attenuation of light 26 increases with a larger separation d, because less light 26 is transmitted through the aperture 32. Although a maximum angle Φ of 50 degrees is shown and described, it is to be understood that the lens assembly 38 can be constructed to produce a different optimum angle.

The light 24 reflected from the first surface 14 may include both specular reflected light 44 and diffuse scattered light 46, sometimes referred to as bright field and dark field light, respectively. The specular light 44 can be detected by the first detector 34. The diffuse light 46 can be reflected by a pin-hole mirror 48 to the second detector 36. The first detector 34 may be a quadcell detector that contains four individual light detectors 50. The second detector 36 may be a photo-multiplier tube.

The detectors 34 and 36 may be connected to a controller 52. The controller 52 may include electronic circuits that can process output signals from the detectors 34 and 36. The controller 52 can process the signals to determine certain surface characteristics of the substrate 12. The surface characteristics may be defects such as bumps or pits. By way of example, the controller 52 may contain circuits and operate in accordance with the processes described in U.S. Pat. No. 5,875,029 issued to Jann et al., which is hereby incorporated by reference.

The substrate 12 may be rotated by a spindle 54 that is mounted to a table 56. The substrate 12 may also move relative to the light beam 20 so that the system 10 can inspect the entire first surface 14. Alternatively, the optics of the system 10 may be moved relative to the substrate 12. The system 10 may also have an automatic loader (not shown) that loads and unloads the substrate 12. The loader may allow inspection of the first surface 14 and then flip the substrate 12 over to inspect the second surface 16.

Figure 3:
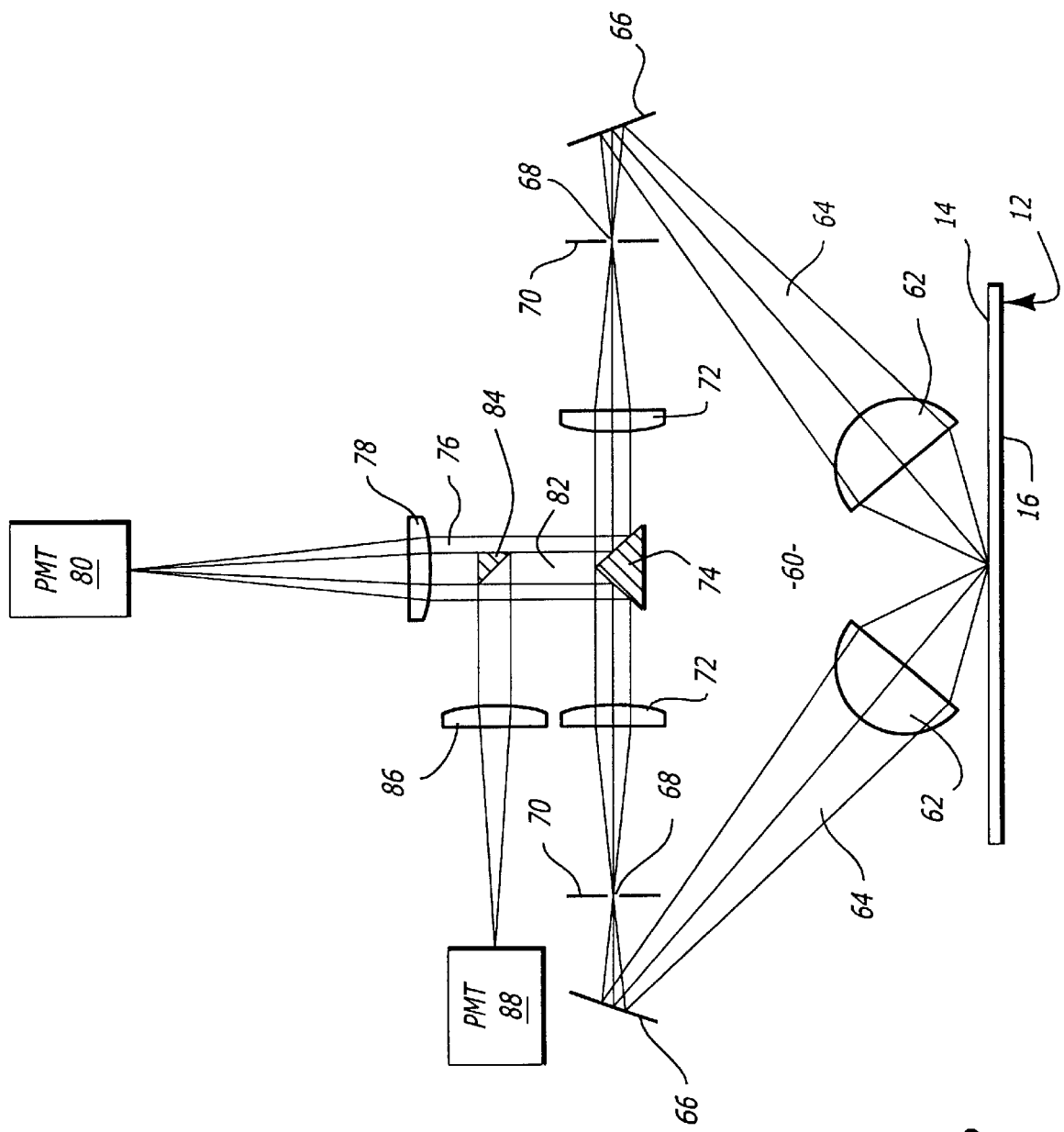
FIG. 3 is a schematic showing a system for detecting light scattered from the substrate.

FIG. 3 shows an additional optical system 60 that can detect light scattered from the substrate 12. This light is sometimes referred to as double dark field. The system 60 may be incorporated into the inspection system 10 depicted in FIG. 1. The system 60 is shown without the other elements of the inspection system 10 to simplify the drawing.

The optical system 60 may include a pair of lenses 62 that direct light 64 scattered from the substrate 12 onto a pair of mirrors 66. The mirrors 66 reflect the light 64 through the apertures 68 of stops 70. Lenses 72 direct the light 64 onto a mirror 74. An outer portion of light 76 reflected from the mirror 74 is focused by lens 78 onto a first scattered light detector 80. An inner portion of light 82 is reflected by mirror 84 and focused by lens 86 onto a second scattered light detector 88. The light detectors 80 and 88 may be photo-multiplier tubes.

The light detectors 80 and 88 can be connected to the controller 52 shown in FIG. 1. The controller 52 can use the input from the light detectors 80 and 88 to determine certain surface characteristics of the substrate 12. For example, the presence of a predetermined level of scattered light may be an indication that the substrate has a particle or other contaminant on the top surface 14. The stops 70 may filter out light scattered from the second surface 16 of the substrate 12 to reduce the optical noise of the system. Although the stops 70 are shown and described, it is to be understood that the system 60 may be used without the stops 70.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An optical inspection system for inspecting a substrate that has a first surface and a second surface, wherein the first surface has a surface characteristic, comprising:

a light source that reflects light from the first surface and the second surface;

a spatial filter that filters light reflected from the second surface;

a first light detector that detects light reflected from the first surface;

a controller that is coupled to said first light detector and can determine the surface characteristic from the detected light;

an optical stop that has an aperture and allows light reflected from the first surface to travel to said first light detector; and, a lens that directs light reflected from the first surface through said aperture and light reflected from the second surface onto said stop.

2. The optical inspection system of claim 1, wherein said light source directs light onto the substrate at an oblique angle.

3. The optical inspection system of claim 1, further comprising a second light detector that detects light reflected from the first surface.

4. The optical inspection system of claim 1, further comprising a spindle that can rotate the substrate.

5. An optical inspection system for inspecting a substrate that has a first surface and a second surface, wherein the first surface has a surface characteristic, comprising:

a spindle that rotates the substrate;

a light source that reflects light from the first surface and the second surface of the substrate, the light reflected from the first surface includes specular reflected light and diffuse scattered light;

a spatial filter that filters light reflected from the second surface;

a first detector that detects specular reflected light;

a second light detector that detects diffuse scattered light;

a controller that is coupled to said first and second light detectors and can determine the surface characteristic from the detected light;

an optical stop that has an aperture that allows light reflected from the first surface to travel to said first and second light detectors; and, a lens that directs light reflected from the first surface through said aperture and light reflected from the second surface onto said stop.

6. The optical inspection system of claim 5, wherein said light source directs light onto the substrate at an oblique angle.

7. The optical inspection system of claim 5, further comprising a first scattered light detector that detects light scattered from the top surface of the substrate.

8. The optical inspection system of claim 7, further comprising a scattered spatial filter that filters light scattered from the second surface of the substrate.

9. A method for inspecting a substrate that has a first surface and a second surface, wherein the first surface has a surface characteristics, comprising:

reflecting and focusing light from the first surface through a stop, and from the second surface onto the stop;

filtering light reflected from the second surface;

detecting light reflected from the first surface; and, determining the surface characteristics from the detected light.

10. The method of claim 9, wherein light is directed onto the substrate at an oblique angle.

11. The method of claim 9, detecting specular reflected light and diffuse scattered light reflected from the first surface.

* * * * *